(12) United States Patent
Kroll et al.

(10) Patent No.: US 7,565,195 B1
(45) Date of Patent: Jul. 21, 2009

(54) FAILSAFE SATELLITE PACEMAKER SYSTEM

(75) Inventors: Mark W. Kroll, Simi Valley, CA (US); Eric S. Fain, Menlo Park, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 509 days.

(21) Appl. No.: 11/104,383

(22) Filed: Apr. 11, 2005

(51) Int. Cl.
*A61N 1/00* (2006.01)
(52) U.S. Cl. .......................................................... 607/2
(58) Field of Classification Search ................ 607/2–9, 607/33, 36, 37; 128/903
See application file for complete search history.

(56) References Cited

U.S. PATENT DOCUMENTS

| | | | |
|---|---|---|---|
| 4,256,115 A | 3/1981 | Bilitch | 128/419 P |
| 4,886,064 A | 12/1989 | Strandberg | 128/419 PG |
| 4,987,897 A | 1/1991 | Funke | 128/419 PG |
| 5,243,977 A | 9/1993 | Trabucco et al. | 607/10 |
| 5,318,594 A * | 6/1994 | Limousin et al. | 607/9 |
| 5,411,535 A | 5/1995 | Fujii et al. | |
| 5,718,235 A * | 2/1998 | Golosarsky et al. | 600/515 |
| 5,814,089 A | 9/1998 | Stokes et al. | 607/32 |
| 6,141,588 A * | 10/2000 | Cox et al. | 607/9 |
| 6,144,879 A | 11/2000 | Gray | 607/20 |
| 6,572,557 B2 | 6/2003 | Tchou et al. | 600/483 |
| 6,645,153 B2 | 11/2003 | Kroll et al. | 600/481 |
| 6,751,503 B1 | 6/2004 | Kroll | 607/18 |
| 7,200,437 B1 | 4/2007 | Nabutovsky et al. | |
| 2001/0049543 A1 | 12/2001 | Kroll | 607/28 |
| 2002/0120318 A1 | 8/2002 | Kroll et al. | 607/149 |

OTHER PUBLICATIONS

NonFinal Office Action, mailed Nov. 20, 2007: Related U.S. Appl. No. 11/104,382.
Final Office Action, mailed Apr. 24, 2008: Related U.S. Appl. No. 11/104,382.
Advisory Action, mailed Jun. 18, 2008: Related U.S. Appl. No. 11/104,382.
Final Office Action, mailed Sep. 19, 2008: Related U.S. Appl. No. 11/104,382.
Final Office Action, mailed Jan. 29, 2009: Related U.S. Appl. No. 11/104,382.

* cited by examiner

*Primary Examiner*—George Manuel

(57) ABSTRACT

In one implementation, a failsafe method for implantable satellite pacemaker pacing is provided, which includes pacing with a satellite pacemaker and monitoring for a local pacing pulse with an other satellite pacemaker. This implementation further includes, pacing with a surrogate satellite pacemaker if the local pacing pulse is not detected by the other satellite pacemaker. Certain implementations may include transmitting a wireless signal from the other satellite pacemaker to a master pacemaker if the local pacing pulse is not detected by the other satellite pacemaker and using the master pacemaker to select the surrogate satellite pacemaker. Certain implementations may include monitoring for the local pacing pulse with a plurality of satellite and causing the plurality of satellite pacemakers to select the surrogate satellite pacemaker.

22 Claims, 10 Drawing Sheets

FAILSAFE SATELLITE PACEMAKER SYSTEM

CROSS-REFERENCE TO RELATED APPLICATIONS

This application is related to copending U.S. patent application Ser. No. 11/104,382, titled "Failsafe Satellite Pacemaker System", filed concurrently herewith.

BACKGROUND

Clinical evidence is revealing that patients suffering from cardiac diseases which affect the contractility of the heart muscle tissue rather than the conduction pathways, generally known as congestive heart failure or CHF, can also benefit from cardiac pacing. CHF is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Treatment typically involves pacing on both sides of the heart. In such patients, pacing in the atria and ventricles effectively resynchronizes heart chamber contractions thereby improving hemodynamic function of the heart. Biventricular pacing has proven to be an effective therapy or treating patient with congestive heart failure.

A system and method for monitoring progression of cardiac disease state using physiologic sensors is disclosed in U.S. Pat. No. 6,572,557, by Tchou, et al., issued Jun. 3, 2003, which describes a technique for monitoring physiological parameters associated with the progression, stabilization, or regression of symptoms of heart disease such as congestive heart failure (CHF), which is herein incorporated by reference in its entirety. A system and method for evaluating risk of mortality due to congestive heart failure using physiologic sensors is disclosed in U.S. Pat. No. 6,645,153 by Kroll et al., issued Nov. 11, 2003, which is herein incorporated by reference in its entirety. One method and apparatus for biventricular stimulation and capture monitoring is disclosed in published U.S. Patent application publication number 20010049543, filed May 1, 2001, by Mark Kroll, herein incorporated by reference in its entirety.

Unfortunately, when fitting a patient with an implantable pacing device, it can be difficult to pass a left-side lead into the coronary sinus vein, or the smaller final destination veins, or keep it in stable position. Accordingly, there is a need for alternative techniques of placing a pacing stimulus on the left side of the heart.

SUMMARY

In one embodiment, an implantable failsafe pacemaker system is provided which includes a master pacemaker and a satellite pacemakers adapted to be mounted to an exterior of a heart. The satellite pacemakers are capable of sensing and delivering pacing pluses to the heart via at least one electrode. The satellite pacemakers include control circuitry adapted to detect the absence of a local pacing pulse during a selected interval and to pace as a surrogate satellite pacemaker if the local pacing pulse is not detected. The control circuitry may be adapted to generate a wireless signal to the master pacemaker if the local pacing pulse is not detected during the selected interval.

In certain embodiments, the control circuitry is adapted to generate a wireless signal to the master pacemaker if the local pacing pulse is not detected during the selected interval and to pace as a surrogate satellite pacemaker if a pace command from the master pacemaker is received in response to the wireless signal to the master pacemaker. In certain embodiments, the control circuitry is adapted to wait for a wireless signal from the master pacemaker to begin pacing as the surrogate satellite pacemaker. In some embodiments, the control circuitry is adapted to cause the satellite pacemakers to select the surrogate satellite pacemaker.

In some embodiments, an implantable failsafe pacemaker system is provided including multiple satellite pacemakers adapted to be mounted to an exterior of a heart. Each satellite pacemaker is capable of sensing and delivering pacing pluses to the heart via at least one electrode. Each satellite pacemaker may include control circuitry configured to wait a unique delay period beyond an escape interval and to begin pacing if no local pacing pulse is detected during the escape interval or the unique delay period.

Certain embodiments of the satellite pacemakers have a random number generator to provide the unique delay period. Other embodiments of the satellite pacemakers have preprogrammed unique delay periods.

In some embodiments, the satellite pacemakers further include wireless transceivers and are configured so that when one satellite pacemaker begins pacing, it transmits information based on its anticipated longevity to the other satellite pacemakers via a wireless communication. The satellite pacemakers may be adapted to enter a low power state in response to the wireless communication.

Further embodiments may include a pacemaker having leads adapted for implantation within a right side of a heart, with the satellite pacemakers being adapted to be attached to a left side of the heart.

In one implementation a failsafe method for implantable satellite pacemaker pacing is provided. The method may include monitoring with each of a plurality of satellite pacemakers for pacing pulses during an escape interval. Thereafter, waiting beyond the escape interval for a unique delay period for each of the satellite pacemakers before attempting to deliver a pacing pulse. If no pacing pulse has been detected during the escape interval and the unique delay period, the satellite pacemaker that has the shortest unique delay period delivers pacing pulses.

In some implementations a failsafe method for implantable satellite pacemaker pacing is provided which includes pacing with a satellite pacemaker and monitoring for a local pacing pulse with at least one other satellite pacemaker. The method further includes pacing with a surrogate satellite pacemaker if the local pacing pulse is not detected by the other satellite pacemaker.

In certain implementations, monitoring for the local pacing pulse includes monitoring with a plurality of satellite pacemakers for the local pacing pulse and generating a wireless signal to a master pacemaker from the other satellite pacemaker if the other satellite pacemaker does not detect the local pacing pulse during a selected interval. The method further includes monitoring for a wireless signal from the master pacemaker assigning pacing responsibility to the surrogate satellite pacemaker.

Certain implementations further include causing the other satellite pacemaker to monitor for a turn-on command from the master pacemaker after generating the wireless signal to the master pacemaker, and causing the other satellite pacemaker to begin pacing as the surrogate satellite pacemaker in response to receiving the turn-on command from the master pacemaker.

In some implementations, generating the wireless signal comprises generating a short burst signal to the master pacemaker. In further implementations, this may include selecting the at least one other pacemaker as the surrogate satellite pacemaker by generating a wireless signal from the master pacemaker in response to the short burst signal.

In some implementations, pacing may continue with the surrogate satellite pacemaker until a battery in the surrogate satellite pacemaker is depleted.

DESCRIPTION

Figure 1:
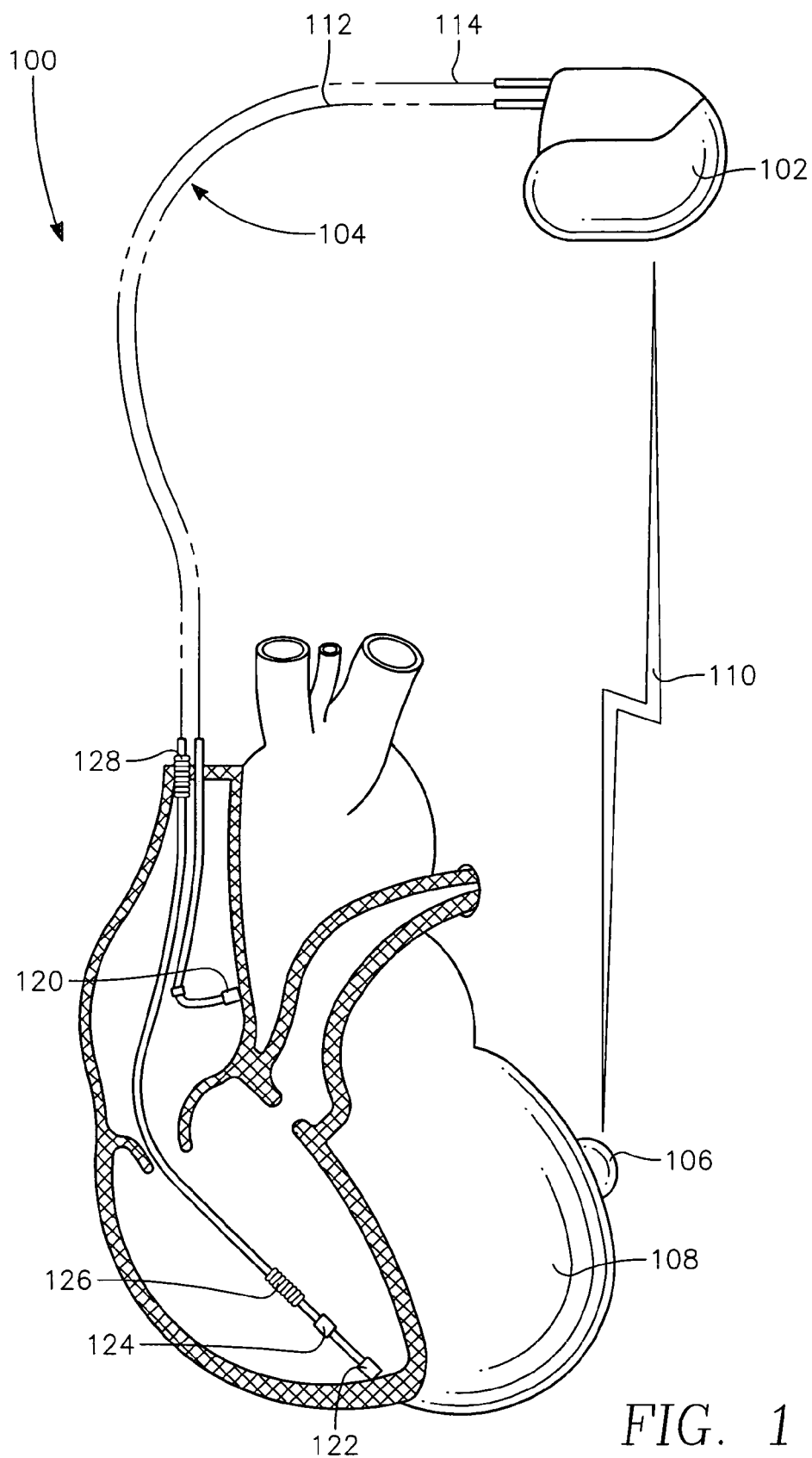
FIG. 1 is a diagrammatic illustration of an implantable cardiac system mounted in electrical communication with a patient's heart for sensing and multi-chamber stimulation therapy.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Leadless Pacemakers

Leadless pacemakers have been described as an alternative to conventional pacemakers. Such systems, though, present problems with longevity and are not always a practical alternative to conventional pacemakers.

Examples of leadless pacemakers are described in issued U.S. Pat. Nos. 5,814,089, by Stokes, et al., entitled LEADLESS MULTISITE IMPLANTABLE STIMULUS AND DIAGNOSTIC SYSTEM, issued 5,814,089; and in issued U.S. Pat. No. 6,141,588, by Cox et al., entitled CARDIAC SIMULATION SYSTEM HAVING MULTIPLE STIMULATORS FOR ANTI-ARRHYTHMIA THERAPY; issued Oct. 31, 2000, both herein incorporated by reference in their entireties. Disclosed is a main control unit, also referred to as a planet, with multiple satellite devices for sensing and stimulating. The planet and satellites communicate wirelessly. The planet processes signals received from the network of satellites and determines if an arrhythmia has occurred by comparing sensed values presented by the network of satellite to a template of normal values. All needed power for the satellites is derived from electromagnetic signals transmitted from the planet. Accordingly, the planet provides electrical energy to operate the satellites.

A drawback with these devices is that they are impractical. Due to the extreme size constraints of the satellite units, combined with the fact that the satellite units are responsible for all the pacing, the battery life is short for the satellite units. To improve longevity of the satellite units, the above described patents anticipate directly recharging the satellite units, wirelessly from the main control unit. Supplying the recharging energy wirelessly from the main control unit, however, is inefficient. Consequently, a practical size implantable parent unit, with sufficient energy to supply the satellites units, would have less than one year longevity.

One practical alternative to the above discussed leadless pacemakers is disclosed by the present inventor in U.S. patent application Ser. No. 10/408,198, filed on Apr. 3, 2003, entitled IMPLANTABLE CARDIAC SYSTEM WITH MASTER PACING UNIT, LEAD ASSEMBLY, AND LEADLESS SLAVE PACING UNIT, herein incorporated by reference in its entirety. In this approach an implantable cardiac system has a master pacing unit and a remote slave pacing unit. The master pacing unit is electrically coupled to a right side of a patients hear via a lead assembly, while the slave pacing unit is a leadless device mounted on the left side of the patient's heart. The slave pacing unit is remotely controlled by the master pacing unit. The two units communicate via a wireless communication link. The master pacing unit delivers right chamber pacing via the lead assembly, while the slave pacing unit delivers left chamber pacing in response to control signals received from the master pacing unit and/or sensing artifacts caused by the right chamber pacing.

Disclosure of U.S. patent application Ser. No. 10/408,198 (FIGS. 1-6)

In the following discussion, an implantable cardiac system is described that treats patients with congestive heart failure (CHF) (see, e.g., NYHA classifications for CHF). The implantable cardiac system has a master pacing unit that applies pacing pulses to the right side of the heart via a lead assembly, and a remote leadless slave pacing unit that applies pacing pulses to the left side of the heart under the direction of the master pacing unit.

Implantable Cardiac System

FIG. 1 shows an exemplary implantable cardiac system 100 having a master pacing unit 102, a lead assembly 104, and a remote leadless slave pacing unit 106. The implantable cardiac system 100 supports multi-chamber detection and stimulation therapy, including biventricular pacing to treat a patient with CHF. The lead assembly 104 interconnects the master pacing unit 102 with the right side of the patient's heart 108. The slave pacing unit 106 is mounted on the left side of the heart, and particularly to the left ventricle. The slave pacing unit 106 can be mounted, for example, using prophylactic techniques during bypass surgery or using a thoracoscopic procedure during implant of the master pacing unit 102. The slave pacing unit 106 communicates with the master pacing unit 102 using wireless communication technologies, such as high frequency modulation, as represented by link 110.

In the illustrated implementation, the lead assembly 104 has two right-sided leads: a right atrial lead 112 and a right ventricular lead 114. The right atrial lead 112 supports an atrial tip electrode 120, which is implanted in the patient's right atrial appendage. The right atrial lead 112 enables the master pacing unit 102 to sense atrial cardiac signals and apply pacing therapy to the right atrial chamber.

The right ventricular lead 114 is electrically coupled to a right ventricular tip electrode 122, a right ventricular ring electrode 124, a right ventricular (RV) coil electrode 126, and an SVC (superior vena cava) coil electrode 128. The right ventricular lead 114 is transvenously inserted into the heart 108 to place the right ventricular tip electrode 122 in the right ventricular apex so that the RV coil electrode 126 will be positioned in the right ventricle and the SVC coil electrode 128 will be positioned in the superior vena cava. Accordingly, the right ventricular lead 114 is capable of receiving cardiac signals, and delivering stimulation in the form of pacing and shock therapy to the right ventricle. It is noted that the RV coil electrode 126 is optional, and may not be present in certain low voltage implementations. While the slave unit cannot deliver high voltage (HV) shock therapy, it can contribute to HV shock therapy by enabling better detection of arrhythmias. By noting an irregularity between the EGM seen by the slave unit and the RV lead, one can detect fibrillation with confidence.

The leadless slave pacing unit 106 is positioned on the left ventricle of the heart 108. It is capable of administering left chamber pacing therapy under the direction of the master pacing unit 102. The slave pacing unit 106 may also be equipped with sensing circuitry to sense artifacts generated by the master pacing unit during right side pacing. In one implementation, the slave pacing unit 106 applies pacing pulses in response to commands communicated from the master pacing unit 102. In another implementation, the slave pacing unit 106 senses the master artifacts and applies pacing pulses in response. In yet another implementation, the slave pacing unit 106 applies pacing pulses in response to a combination of sensed master artifacts and commands from the master pacing unit.

Although not illustrated, the implantable cardiac system 100 may be configured to support more than one remote slave pacing unit. A physician may elect to mount multiple slave pacing units 106 at different positions of the heart. The physician is then able to evaluate various slave pacing units 106 to determine which one is most effective at applying the pacing pulses. In another technique, the physician might elect to implant multiple slave pacing units in physical proximity, initially turning all units off. Then, after implantation, the physician can activate the slave pacing units one at a time, as needed, as units run low on batteries or experience problems that preclude effective operation (e.g., electrode dislodgment).

As another alternate configuration, the system 100 can be configured to support triple timing optimal ventricular pacing to obtain optimal hemodynamics. For example, one slave unit is placed 1 cm down from the ventricular base by the lateral cardiac vein while a second slave is placed 3 cm down by the same vein. Then, the first slave unit is paced and the second is paced 10 ms later, and finally, the RV tip electrode is paced another 15 ms later. Similarly, this is extendable to 4 or more left sided slave units.

Figure 2:
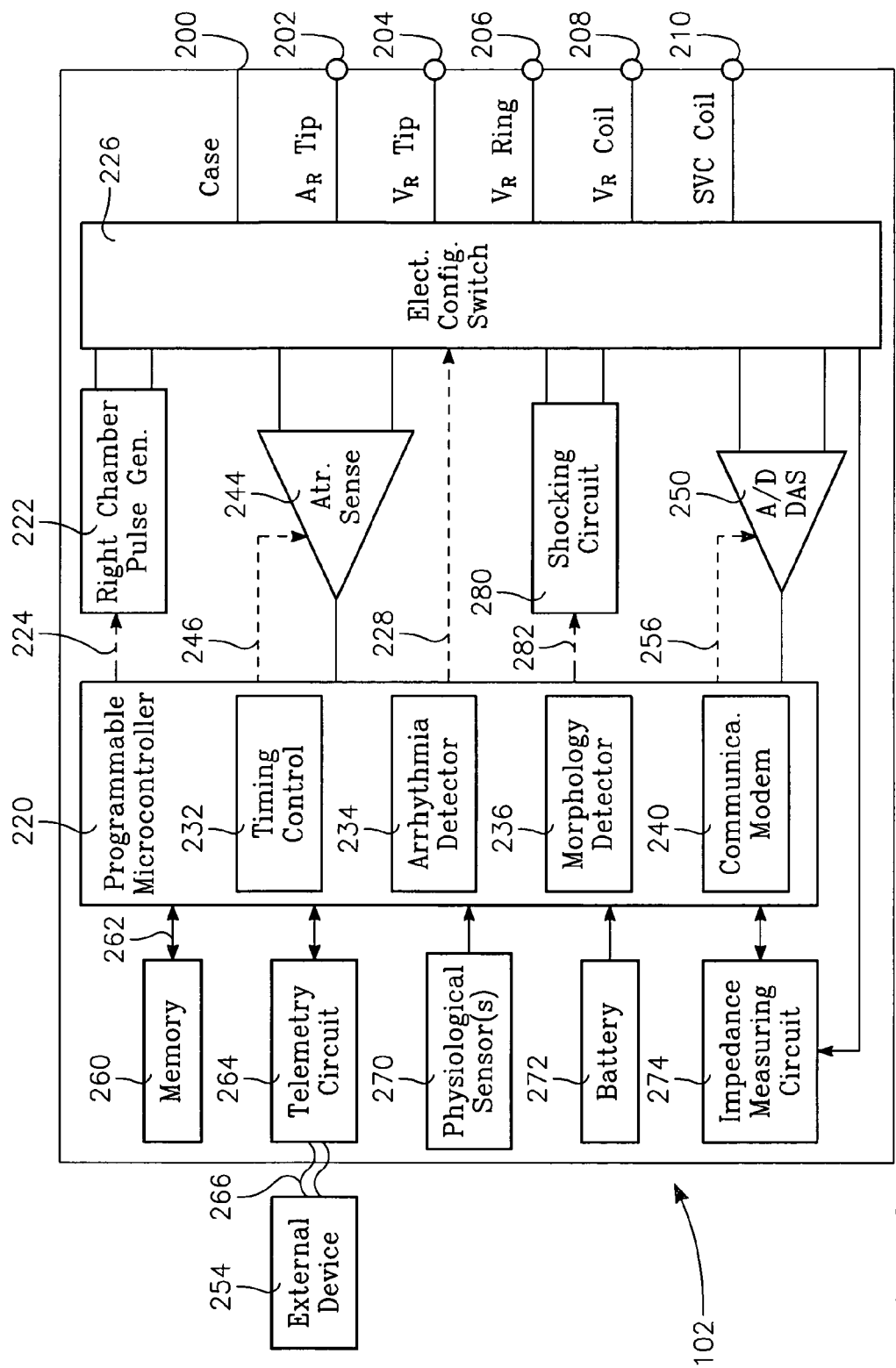
FIG. 2 is a block diagram of a master pacing unit employed in the implantable cardiac system.

It is further noted that the remote pacing units can be put in hibernation upon transmission of a deactivation signal from the master pacing unit, or on command of an external programmer (not shown in FIG. 1, but illustrated in FIG. 2).

Exemplary Master Pacing Unit

FIG. 2 shows an exemplary master pacing unit 102 that is implanted into the patient as part of the implantable cardiac system 100. The master pacing unit 102 may be implemented as a full-function biventricular pacemaker, equipped with both atrial and ventricular sensing and pacing circuitry for four chamber sensing and stimulation therapy (including both pacing and shock treatment). Alternatively, the master pacing unit 102 may be implemented with a reduced set of functions and components. For instance, the master pacing unit may be implemented without ventricular sensing and pacing because such functions can be implemented at the remote slave pacing unit 106. For discussion purposes, this latter reduced-function implementation will be described.

The master pacing unit 102 has a housing 200 to hold the electronic/computing components. The housing 200 (which is often referred to as the "can", "case", "encasing", or "case electrode") may be programmably selected to act as the return electrode for certain pacing modes. Housing 200 further includes a connector (not shown) with a plurality of terminals 202, 204, 206, 208, and 210. The terminals are shown schematically and, for convenience, the names of the electrodes to which they are connected are identified. The terminals include:

a right atrial tip terminal (AR TIP) 202 for atrial tip electrode 120;

a right ventricular tip terminal (VR TIP) 204 for right ventricular tip electrode 122;

a right ventricular ring terminal (VR RING) 206 for right ventricular ring electrode 124;

a right ventricular shocking terminal (VR COIL) 208 for right ventricular coil electrode 126; and an SVC shocking terminal (SVC COIL) 210 for SVC coil electrode 128.

The master pacing unit 102 includes a programmable microcontroller 220 that controls various operations of the master pacing unit 102, including cardiac monitoring and stimulation therapy. Microcontroller 220 includes a microprocessor (or equivalent control circuitry), RAM and/or ROM memory, logic and timing circuitry, state machine circuitry, and I/O circuitry.

Master pacing unit 102 further includes a right chamber pulse generator 222 that generates pacing stimulation pulses for delivery by the right atrial lead 112 and/or the right ventricular lead 114 to the right chambers of the heart. The pulse generator 222 is controlled by the microcontroller 220 via control signal 224. The right chamber pulse generator 222 is coupled to the lead assembly 104 via an electrode configuration switch 226, which includes multiple switches for connecting the desired electrodes to the appropriate I/O circuits, thereby facilitating electrode programmability. The switch 226 is controlled by a control signal 228 from the microcontroller 220.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector 236.

Although not shown, the microcontroller 220 may further include other dedicated circuitry and/or firmware/software components that assist in monitoring various conditions of the patient's heart and managing pacing therapies.

The master pacing unit 102 is further equipped with a communication modem (modulator/demodulator) 240 to enable wireless communication with the remote slave pacing unit 106. In one implementation, the communication modem 240 uses high frequency modulation. As one example, the modem 240 transmits signals between a pair of electrodes of the lead assembly 104, such as between the can 200 and the right ventricular tip electrode 122. The signals are transmitted in a high frequency range of approximately 20-80 kHz, as such signals travel through the body tissue in fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The master pacing unit 102 has right chamber sensing circuitry 244 selectively coupled to the right atrial lead 112 and the right ventricular lead 114 through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and a threshold detection circuit to selectively sense the cardiac signal of interest. The automatic gain control enables the unit 102 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the right chamber sensing circuitry 244 is connected to the microcontroller 220 which, in turn, triggers or inhibits the right chamber pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

The master pacing unit 102 further includes an analog-to-digital (A/D) data acquisition system (DAS) 250 coupled to the lead assembly 104 via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the master pacing unit 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 108 within each respective tier of therapy.

The operating parameters of the master pacing unit 102 may be non-invasively programmed into the memory 260 through a telemetry circuit 264 in telemetric communication via communication link 266 with the external device 254. The telemetry circuit 264 allows intracardiac electrograms and status information relating to the operation of the master pacing unit 102 (as contained in the microcontroller 220 or memory 260) to be sent to the external device 254 through the established communication link 266.

The master pacing unit 102 can further include magnet detection circuitry (not shown), coupled to the microcontroller 220, to detect when a magnet is placed over the unit. A magnet may be used by a clinician to perform various test functions of the unit 102 and/or to signal the microcontroller 220 that the external programmer 254 is in place to receive or transmit data to the microcontroller 220 through the telemetry circuits 264.

The master pacing unit 102 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 102, the physiologic sensor(s) 270 may be external to the unit 102, yet still be implanted within or carried by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the master pacing unit 102. The battery 272 is capable of operating at low current drains for long periods of time (e.g., less than 10 □A), and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 102 employs lithium/silver vanadium oxide batteries.

The master pacing unit 102 further includes an impedance measuring circuit 274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The master pacing unit 102 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart 108 through shocking electrodes selected, for example, from the right atrial coil electrode 126 and the SVC coil electrode 128. It is noted that the shock therapy circuitry is optional and may not be implemented in the master pacing unit, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the master pacing unit.

The master pacing unit 102 can be programmed to treat CHF by applying pacing to the right atrial and right ventricle via leads 112 and 114 and communicating with the remote slave pacing unit 106 to pace the left ventricle. One or more slave pacing units can be operated under the control of the master pacing unit 102. Different implementations of the slave pacing units are described next.

Exemplary Slave Pacing Units

The slave pacing unit 106 is implanted into the patient as part of the implantable cardiac system 100 and preferably mounted on or proximal to the left ventricle. The slave pacing unit 106 may be implemented in many ways, depending upon the functionality desired in the remote unit. The unit may be configured as complex as a full-function pacemaker with multi-chamber sensing and pulse generation capabilities, or more simply with a reduced set of functionality. Three exemplary implementations are described.

Passive Slave

Figure 3:
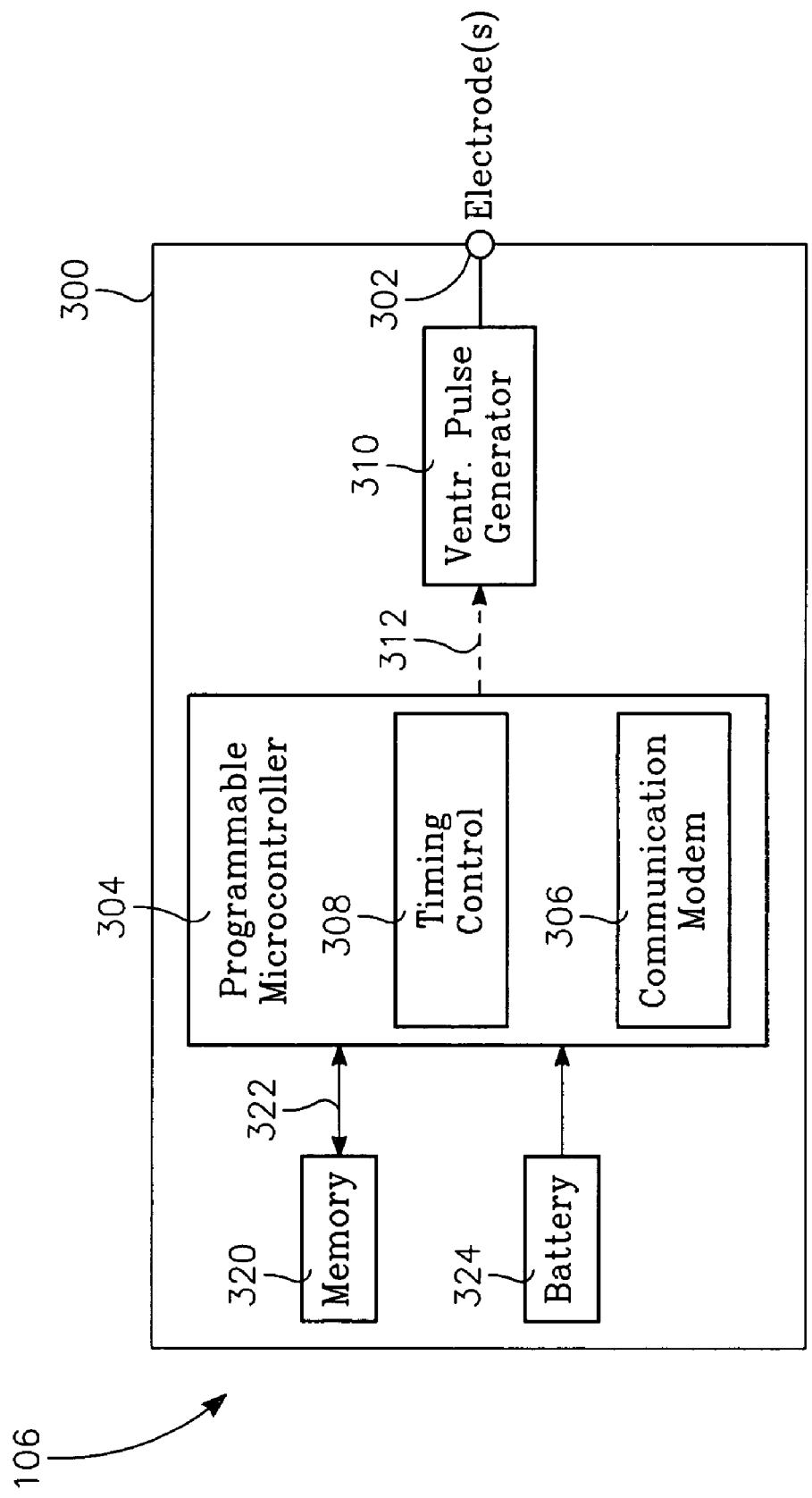
FIG. 3 is a block diagram of a first implementation of a slave pacing unit employed in the implantable cardiac system.

FIG. 3 shows one exemplary slave pacing unit 106 that has minimal functionality. In this example, the slave pacing unit 106 is configured as a simple passive device that paces the left ventricle in response to commands from the master pacing unit 102. The slave pacing unit 106 has a housing 300 to hold and protect the electronic/computing components. One or more electrodes 302 are mounted in the housing 300 to deliver pacing pulses to the heart tissue. The electrode(s) and/or a separate anchor mechanism can be used to secure the slave pacing unit 106 to the left ventricle, as shown in FIG. 1. In an alternate embodiment, one or more of the electrodes 302 are mounted on one or more leads 303 (shown in phantom in FIG. 1) extending from the housing 300, which allows the one or more electrodes to be spaced from the housing 300. For example, one or more electrodes 302 could be mounted on the housing 300 for placement at a first location (e.g., adjacent to the left atrium), and another electrode or electrodes 302 could be connected to lead 303 for placement at a second location (e.g., adjacent to the left ventricle).

The slave pacing unit 106 includes a programmable microcontroller 304 to control the pacing operation of the slave pacing unit. A communication modem 306 is provided to facilitate wireless communication with the master pacing unit 106 using high frequency modulation. The communication modem 306 may be implemented in hardware as part of the microcontroller 304, or as software/firmware instructions programmed into and executed by the microcontroller 304. Alternatively, the modem may reside separately from the microcontroller as a standalone component. Microcontroller 304 may be further equipped with timing control circuitry 308 to control the timing of the stimulation pulses being applied to the left ventricle in response to command signals received via communication modem 306 from the master pacing unit 102.

The slave pacing unit 106 has a ventricular pulse generator 310 to generate pacing stimulation pulses for delivery by the electrode 302. The ventricular pulse generator 310 is controlled by the microcontroller 304 via control signal 312.

The microcontroller 304 is coupled to a memory 320 via data/address bus 322. Any programmable operating parameters to be used by the microcontroller 304 can be stored in memory 320 and used to customize the operation of the slave pacing unit 106 to suit the needs of a particular patient. Such operating parameters can be programmed into the memory 320 via instructions transmitted from the master pacing unit to the slave pacing unit 106, where they are received at the communication modem 306 and stored in the memory 320. In simpler constructions, where no programmable operating parameters are employed or desired, the memory 320 and bus 322 may be omitted.

The slave pacing unit 106 further includes a battery 324 to supply operating power to all of the components shown in FIG. 3. The battery 324 is capable of operating at low current drains for long periods of time (e.g., less than 10 □A), and is capable of providing pulses of sufficient voltage and current to apply pacing to the heart. As one example, the battery 324 is implemented as one or more lithium/silver vanadium oxide batteries.

In the FIG. 3 configuration, the slave pacing unit 106 delivers a pacing pulse to the patient's left ventricle in response to commands transmitted from the master pacing unit 102. The commands are communicated via the wireless link 110 to the communication modem 306. The commands are processed by the microcontroller 304. Once received and processed, the slave pacing unit 106 passively responds by generating a pacing pulse at the pulse generator 310 and delivering the pulse via the electrode(s) 302. The pulse may be applied immediately, or after some timing delayed dictated by the timing control circuitry 308.

Passive Slave with Sensing Capabilities

Figure 4:
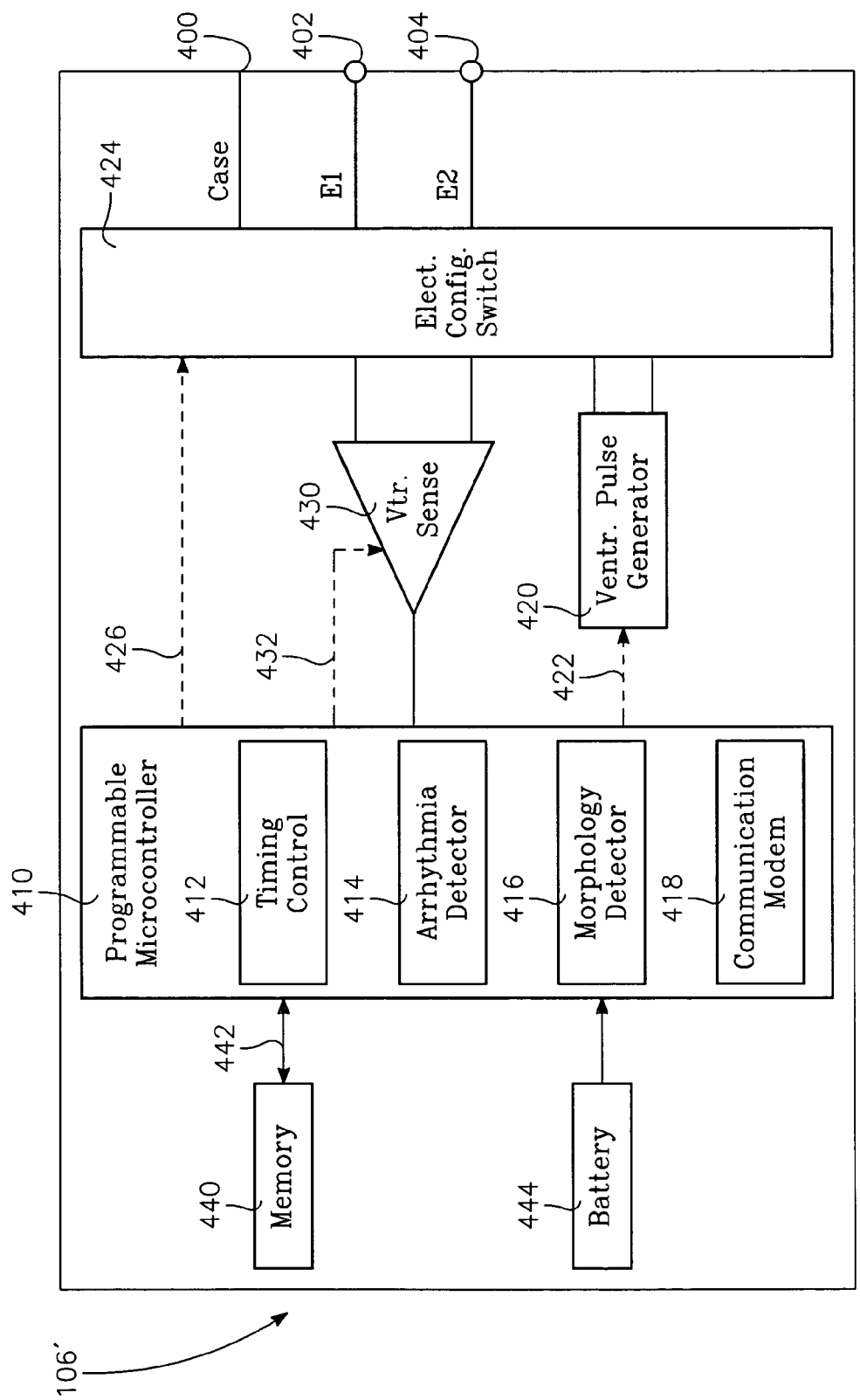
FIG. 4 is a block diagram of a second implementation of a slave pacing unit employed in the implantable cardiac system.

FIG. 4 shows another exemplary slave pacing unit 106', which is implemented more functionality than that of the slave pacing unit 106 of FIG. 3. In this example, the slave pacing unit 106' is configured with sensing capabilities and diagnostic detection capabilities that is more akin to a full-function pacemaker. The slave pacing unit 106' has a housing 400 to hold and protect the electronic/computing components. Housing 400 has a connector (not shown) with a plurality of terminals for connections to associated electrodes. The terminals include a first electrode (E1) 402 and a second electrode (E2) 404. More or less electrodes may be used in other configurations. Since the combination of the central electrode and the housing serve as a sensing dipole, no additional electrodes are needed for sensing and pacing. So, the slave pacing unit 106' could function as a VVI pacemaker. However, with additional electrodes the slave pacing unit 106' could detect other signals (such as far-field P-waves) to allow more sophisticated modes of operation.

The slave pacing unit 106' includes a programmable microcontroller 410 that controls various operations of the pacing unit, including cardiac monitoring and stimulation therapy. Timing control circuitry 412 may be configured to control the timing of the stimulation pulses applied via the electrodes 402 and 404. Together with the timing stipulated by the master pacing unit for the right atrial and right ventricle, the timing control circuitry 412 may be used to time stimulation pulses (e.g., pacing rate, atrio-ventricular (AV) delay, atrial interconduction (A-A) delay, or ventricular interconduction (V-V)

delay, etc.), refractory periods, blanking intervals, noise detection windows, evoked response windows, alert intervals, marker channel timing, and so on.

Microcontroller 410 has an arrhythmia detector 414 for detecting arrhythmia conditions and a morphology detector 416 for detecting morphological-related parameters. The slave pacing unit 106' is further equipped with a communication modem 418 to facilitate wireless communication with master pacing unit 102 using high frequency modulation.

The slave pacing unit 106' further includes a ventricular pulse generator 420 to generate pacing stimulation pulses for delivery by the electrodes 402 and 404 to the left ventricle of the patient's heart. The ventricular pulse generator 420 is controlled by the microcontroller 420 via control signal 422 and is coupled to the leads 400-404 via an electrode configuration switch 424. The switch 424 includes one or more switches for connecting the desired electrodes to the appropriate I/O circuits, thereby providing electrode programmability. The microcontroller 410 controls the switch 424 via a control signal 426.

In the illustrated implementation, the slave pacing unit 106' is equipped with ventricular (VTR. SENSE) sensing circuit 430, which can be selectively coupled to electrodes 402 and 404 to detect the presence of cardiac activity in the left ventricle of the heart. The ventricular sensing circuit 430 may include dedicated sense amplifiers, multiplexed amplifiers, or shared amplifiers. It may employ one or more low power, precision amplifiers with programmable gain and/or automatic gain control, bandpass filtering, and a threshold detection circuit, to selectively sense the cardiac signal of interest. The ventricular sensing circuit 430 is controlled by the microcontroller 410 via control signal 432.

The microcontroller 410 is coupled to a memory 440 via data/address bus 442 to store various programmable operating parameters used to customize operation of the slave pacing unit 106'. Operating parameters can be programmed into the memory 440 via instructions transmitted from the master pacing unit to the slave pacing unit 106', where they are received at the communication modem 418 and stored in the memory 440. The unit 106' further has a battery 444 to provide power to all components in the unit. The battery 444 also provides power for the stimulation pulses.

In the FIG. 4 configuration, the slave pacing unit 106' can deliver pacing pulses to the patient's left ventricle in response to commands transmitted from the master pacing unit 102. This is similar to the slave pacing unit 106 of FIG. 3. Such commands are communicated via the wireless link 110 to the communication modem 418. Once received, the slave pacing unit 106' responds by generating a pacing pulse at the pulse generator 420 and delivering the pulse via the electrode(s) 402 and 404.

Additionally, the slave pacing unit 106' can be configured to deliver pacing pulses in response to detection of a pacing artifact induced by the master pacing unit. The master pacing unit 102 delivers a pacing pulse to the right side of the patient's heart to initiate a contraction. The ventricular sensing circuit 430 resident at the slave pacing unit 106' detects the pacing spike and delivers its own properly timed pacing pulse to the left ventricle. The pacing pulse could be applied instantaneous upon detection of the master pacing pulse, or after some programmed delay. The advantage of the artifact sensing mode of operation is that the programming and communication schemes are easier to implement. A disadvantage of the sensing mode, however, is that the slave pacing unit 106' is unable to pulse before the master pacing unit 102. This disadvantage can be overcome, however, by operating the unit in both the artifact sensing mode and the command-responsive mode, whereby the master pacing unit can send a pacing command directing the slave pacing unit to pace before delivery of the master pacing pulse.

Active Slave

Figure 5:
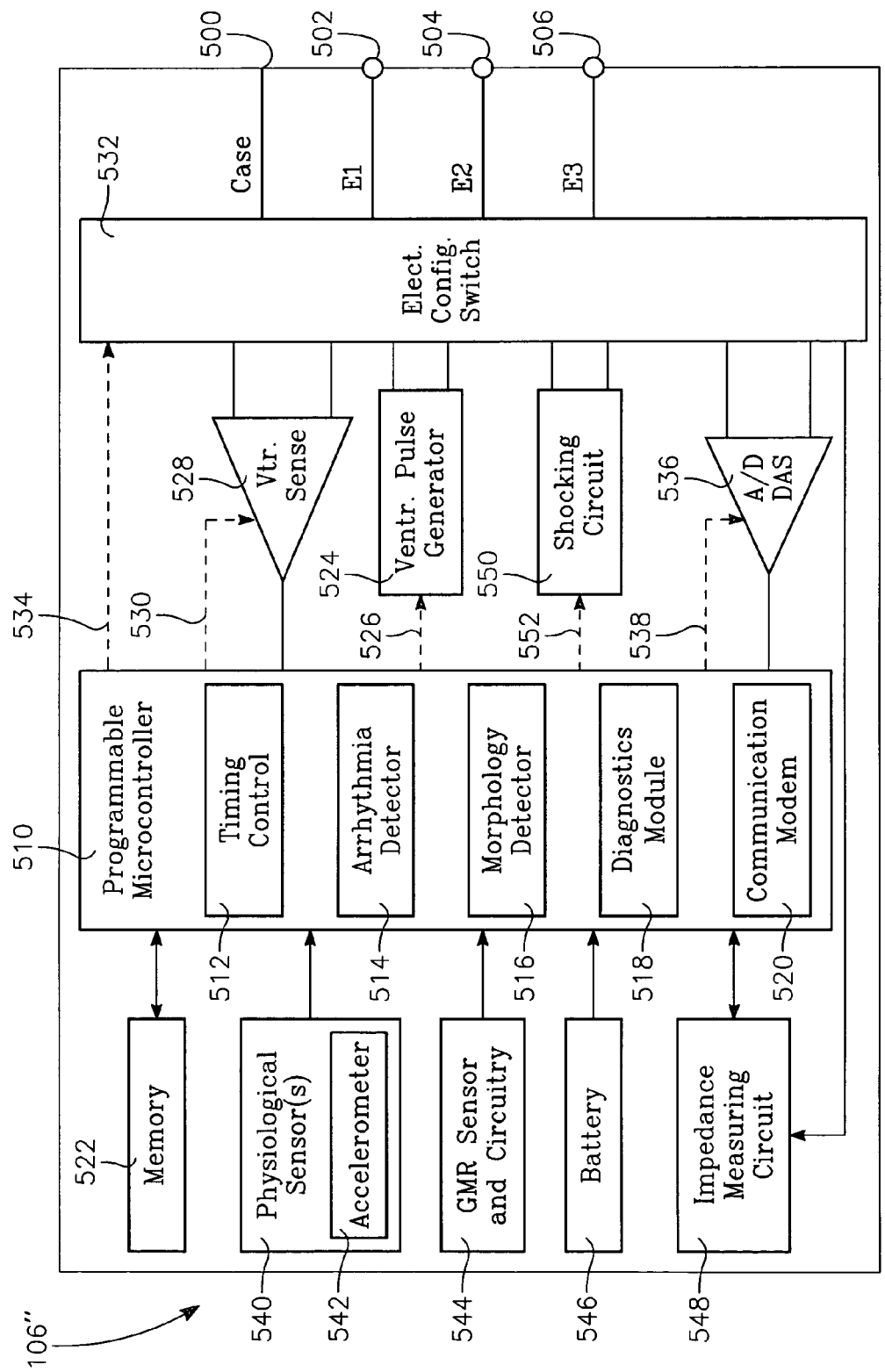
FIG. 5 is a block diagram of a third implementation of a slave pacing unit employed in the implantable cardiac system.

FIG. 5 shows another exemplary slave pacing unit 106" configured as a full-function device capable of sensing, pacing, and diagnostic feedback, as well as two-way communication. The unit 106" includes a housing 500 that supports up to three electrodes: electrode (E1) 502, electrode (E2) 504, and electrode (E3) 506. The unit may be configured to support more or less electrodes in other configurations. The electrodes allow the slave pacing unit 106" to achieve left chamber sensing and pacing. Representative electrodes include a left ventricular tip electrode, and two widely separated point electrodes to sense the far-field atrial signals.

A programmable microcontroller 510 controls various modes of stimulation therapy. It also collects diagnostic information and returns the information to the master pacing unit 102, which may then communicate the information to an external device 254 for review by the physician. The microcontroller 510 includes a microprocessor, or equivalent control circuitry, designed specifically for controlling the delivery of stimulation therapy, and may further include RAM or ROM memory, logic and timing circuitry, state machine circuitry, and I/O circuitry.

Microcontroller 510 includes timing control circuitry 512, an arrhythmia detector 514, a morphology detector 516, a diagnostics module 518, and a communication modem 520. The diagnostics module 518 collects data sensed by the slave pacing unit 106". A memory 522 is coupled to the microcontroller 510 to store the data captured by the slave pacing unit, as well as any operating parameters used by the microcontroller 510.

The communication modem 520 offers both reception and transmission capabilities. In this manner, the communication modem 520 receives command instructions from the master pacing unit 102 via wireless link 110 and uses the instructions for pacing or shock therapies, as well as to alter programming parameters of the microcontroller 510. Additionally, the communication modem 520 can be used to transmit data collected by the slave pacing unit 106" back to the master pacing unit 102 via the wireless link 110. The data may be used by the master pacing unit 102 to identify various conditions and to administer therapies in response. Thus, data collected by the slave pacing unit 106" may be stored locally in memory 522, at the master pacing unit 102, and/or transmitted out to the external device 254 (FIG. 2).

The slave pacing unit 106" has a ventricular pulse generator 524 to generate pacing stimulation pulses for delivery by one or more electrodes 502-506. The microcontroller 510 controls the ventricular pulse generator 524 via a control signal 526. Ventricular sensing circuit 528 is employed to sense the presence of cardiac activity in one or both of the left chambers of the heart. The sensing circuit 528 receives a control signal 530 from the microcontroller 510 for purposes of controlling the gain, threshold, polarization charge removal circuitry, and the timing of any blocking circuitry.

An electronic configuration switch 532 connects the pulse generator 524 and sensing circuit 528 to the desired electrodes. In response to a control signal 534 from the microcontroller 510, the switch 532 makes the proper connections to the electrodes.

The slave pacing unit 106" utilizes the ventricular sensing circuit 528 to sense cardiac activity, including inherent beats and pacing artifacts. Sensed cardiac activity can be used by the arrhythmia detector 514 to classify arrhythmias. Sensed artifacts may be used to trigger pacing in the slave pacing unit, as is described below in more detail.

An analog-to-digital (A/D) data acquisition system (DAS) 536 acquires intracardiac electrogram signals, converts the raw analog data into a digital signal, and stores the digital signals for later processing and/or transmission to the master pacing unit 102. The data acquisition system 536 is coupled to the various electrodes through the switch 532 to sample cardiac signals across desired electrodes. The microcontroller 510 controls operation of the data acquisition system 536 via control signal 538.

The data acquisition system 536 may be used to detect an evoked response from the heart in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 510 detects a depolarization signal during a window following a stimulation pulse, the presence of which indicates that capture has occurred. The microcontroller 220 enables capture detection by triggering the ventricular pulse generator 524 to generate a stimulation pulse, starting a capture detection window using the timing control circuitry 512 within the microcontroller 510, and enabling the data acquisition system 536 via control signal 538 to sample the cardiac signal that falls in the capture detection window and, based on the amplitude, determines if capture has occurred.

The slave pacing unit 106" can further include one or more physiological sensors 540 which may be used to detect changes in cardiac output, changes in the physiological condition of the heart, or diurnal changes in activity (i.e., detecting sleep and wake states). While shown as being included within the unit housing, the physiologic sensors 540 may be external to the housing, yet still be implanted within or carried by the patient. Examples of physiologic sensors include sensors that sense respiration rate, pH of blood, ventricular gradient, and so forth. Another sensor that may be used is one that detects activity variance, wherein an activity sensor is monitored diurnally to detect the low variance in the measurement corresponding to the sleep state.

One specific type of physiological sensor is a three-dimensional (3D) accelerometer-based sensor 542 that measures the acceleration resulting from the patient's movement. The accelerometer can be used to sense a contraction and/or body movement. The signals are passed to the microcontroller 510 for analysis in determining whether the sensed acceleration pertains to a contraction or indicates that the patient is undergoing heightened physical exertion or is moving directionally upwards (e.g., walking upstairs) or downwards (e.g., reclining for sleep or rest). The microcontroller 510 may use the information to adjust the pacing rate or invoke various pacing therapies.

The slave pacing unit 106" may also be equipped with a GMR (giant magnetoresistance) sensor and circuitry 544 that detects the earth's magnetic fields. The GMR sensor and circuitry 544 may be used to ascertain absolute orientation coordinates based on the earth's magnetic fields. The device is thus able to discern a true vertical direction regardless of the patient's position (i.e., whether the patient is lying down or standing up). The three-axis orientation coordinates measured by the 3D accelerometer-based sensor 542 may then be taken relative to the absolute orientation coordinates from the GMR. For instance, as a person sits up, the axial coordinates of the 3D accelerometer-based sensor 544 might change by 90°, but the sensor signals may be calibrated as to the true vertical direction based on the output of the GMR sensor and circuitry 544.

A battery 546 provides operating power to all of the circuits, as well as for the pacing and shocking pulses. For shocking therapy, the battery 546 is capable of operating at low current drains for long periods of time (e.g., preferably less than 10 □A), and is capable of providing high-current pulses (for capacitor charging) when the patient requires a shock pulse (e.g., preferably, in excess of 2 A, at voltages above 2 V, for periods of 10 seconds or more). The battery 546 has a predictable discharge characteristic so that elective replacement time can be detected.

In the case where the remote unit 106" is intended to operate as an implantable cardioverter/defibrillator (ICD) device, the microcontroller 510 detects the occurrence of an arrhythmia and automatically applies an appropriate electrical shock therapy to the heart aimed at terminating the detected arrhythmia. The microcontroller controls a shocking circuit 550 by way of a control signal 552 to generate shocking pulses of low (up to 0.5 joules), moderate (0.5-10 joules), or high energy (11 to 40 joules). The shocking can be applied solely by the remote slave pacing unit 106" or in concert with the master pacing unit 102.

In the FIG. 5 configuration, the slave pacing unit 106" offers a full range of functionality. It can deliver pacing pulses to the patient's left ventricle in response to commands transmitted from the master pacing unit 102. It is also capable of detecting a pacing artifact induced by the master pacing unit and delivering a responsive pacing pulse. Additionally, the remote slave pacing unit can be programmed to a failsafe mode that requires it to (1) sense either an inherent R wave or a pacing spike administered by the master pacing unit, in addition to (2) receiving a pacing command from the master pacing unit. Furthermore, with two-way communication, the slave pacing unit is able to provide diagnostic information to the master pacing unit. The two units could also be configured to cooperate for ventricular fibrillation (VF) detection by noting cross-chamber de-correlation.

Operation

The cardiac system 100 is implanted into a patient for treatment of CHF. The master pacing unit 102 and one or more slave pacing units 106 can be implanted together or at separate times. The master pacing unit is preferably implanted when the patient is to begin pacing therapies. The slave pacing units can be implanted at the same time or some time prior to the master pacing unit.

The one or more slave pacing units can be prophylacticly implanted around the heart. With currently available high-density CFx batteries, for example, the small units are expected to operate for two to five years. The multiple units may be used together, or for backup purposes in the event that certain units fail. For instance, where a high threshold is found at implant on the left side, the physician might choose to implant one or more backup units. The slave pacing units are initially turned off.

Figure 6:
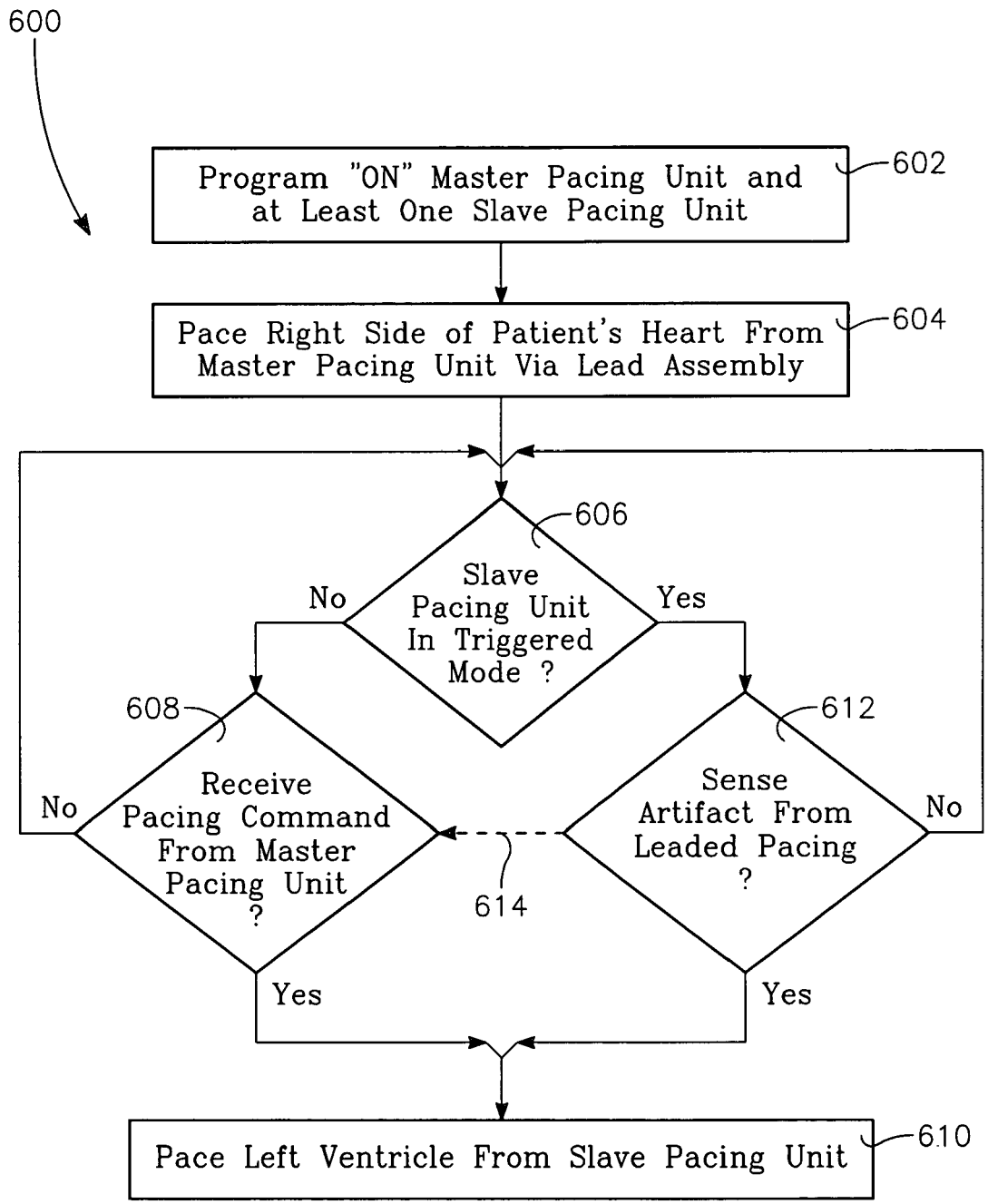
FIG. 6 is a flow diagram of an exemplary process for operating the implantable cardiac system.

FIG. 6 shows a process 600 for operating the implantable cardiac system 100 once implanted. In the flow diagram, the operations are summarized in individual blocks. The operations may be performed in hardware and/or as machine-readable instructions (software or firmware) that can be executed by a processor, such as the microcontrollers used in the pacing units.

At block 602, the master pacing unit 102 and at least one slave pacing unit 106 are programmed on. In one implementation, the external programmer 254 turns on the master pacing unit 102, and the master pacing unit sends an activation signal to activate the slave pacing unit 106. Alternatively, both units are programmed on by the external programmer. Once programmed on, many modes of operation are possible. Two such modes are illustrated for discussion purposes. In a "triggered" mode, the slave pacing unit 106 generates pacing pulses in response to, or triggered off of, the pacing artifact from the master pacing unit's pacing pulse. This mode can be performed by a slave pacing unit that is equipped with sensing circuitry, such as the units 106' (FIG. 4) and unit 106" (FIG. 5). In a non-triggered mode, the slave pacing unit 106 operates under the direct control of the master pacing unit. The mode can be performed by any slave pacing unit described herein in FIGS. 3-5.

At block 604, the master pacing unit 102 paces the right side of the patient's heart via the lead assembly 104.

At block 606, the system determines whether the slave pacing unit 106 is in triggered mode or non-triggered mode. If in non-triggered mode (i.e., the "no" branch from block 606), the slave pacing unit 106 (or 106' or 106") awaits a pacing command from the master pacing unit 102 (block 608). The pacing command directs the slave pacing unit to generate a pacing pulse in coordination with the pacing pulse generated by the master pacing unit. When the pacing command is received (i.e., the "yes" branch from block 606), the slave pacing unit paces the left ventricle (block 610).

If the slave pacing unit is in triggered mode (i.e., the "yes" branch from block 606), it attempts to sense pacing artifacts induced by the master pacing unit 102 (block 612). This pacing artifact indicates that the master pacing unit has applied a pacing pulse to the right side of the heart, which is now being conducted through the left side of the heart. When a pacing artifact is sensed (i.e., the "yes" branch from block 612), the slave pacing unit paces the left ventricle (block 610). One advantage of triggered mode is that the coding and communication scheme is comparatively easy. The slave unit merely detects the pacing spike and delivers its own pacing pulse in response. However, in a purely triggered mode, the slave pacing unit is unable to pulse before the master pacing unit in the right ventricle chamber because it paces in response to the right ventricle pacing. The slave pacing unit either paces simultaneously with the master pacing spike, or following a programmed delay.

The system 100 may be operated in both triggered and non-triggered mode, as represented by the dashed control line 614 which would substitute for the "No" branch from block 612. Additionally, the decision block 606 could be omitted, as both conditions at blocks 608 and 612 would be evaluated. In this dual mode implementation, if the slave pacing unit does not sense an artifact at block 612, it then checks for a pacing command received from the master pacing device (block 608) via control path 614. In this manner, the slave pacing unit can be directed to pace the left side of the heart in response to either sensing a pacing artifact in the heart or receiving a pacing command from the master pacing unit. With this implementation, the master pacing unit can transmit a high frequency pacing command to the slave pacing unit to allow it to pace before the master pulse is delivered.

In another implementation, the slave pacing unit can be programmed to ensure both conditions (i.e., receipt of a pacing command at block 608 and a sensed artifact at block 612) prior to delivering a pacing pulse. This provides a failsafe mode of pacing.

Figure 7:
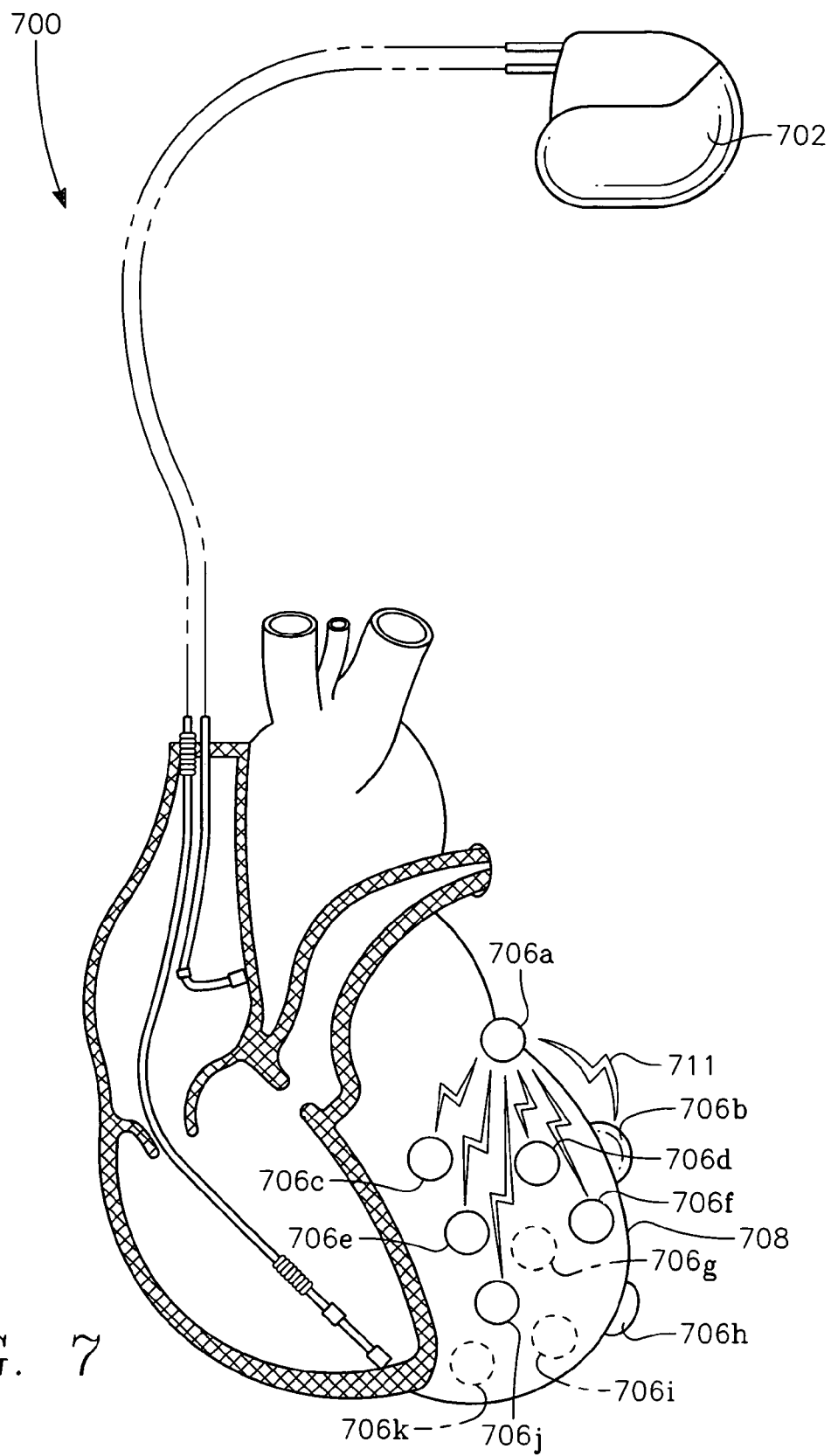
FIG. 7 shows a perspective view of a failsafe satellite pacemaker system in accordance with one possible embodiment of the present invention.
Figure 8:
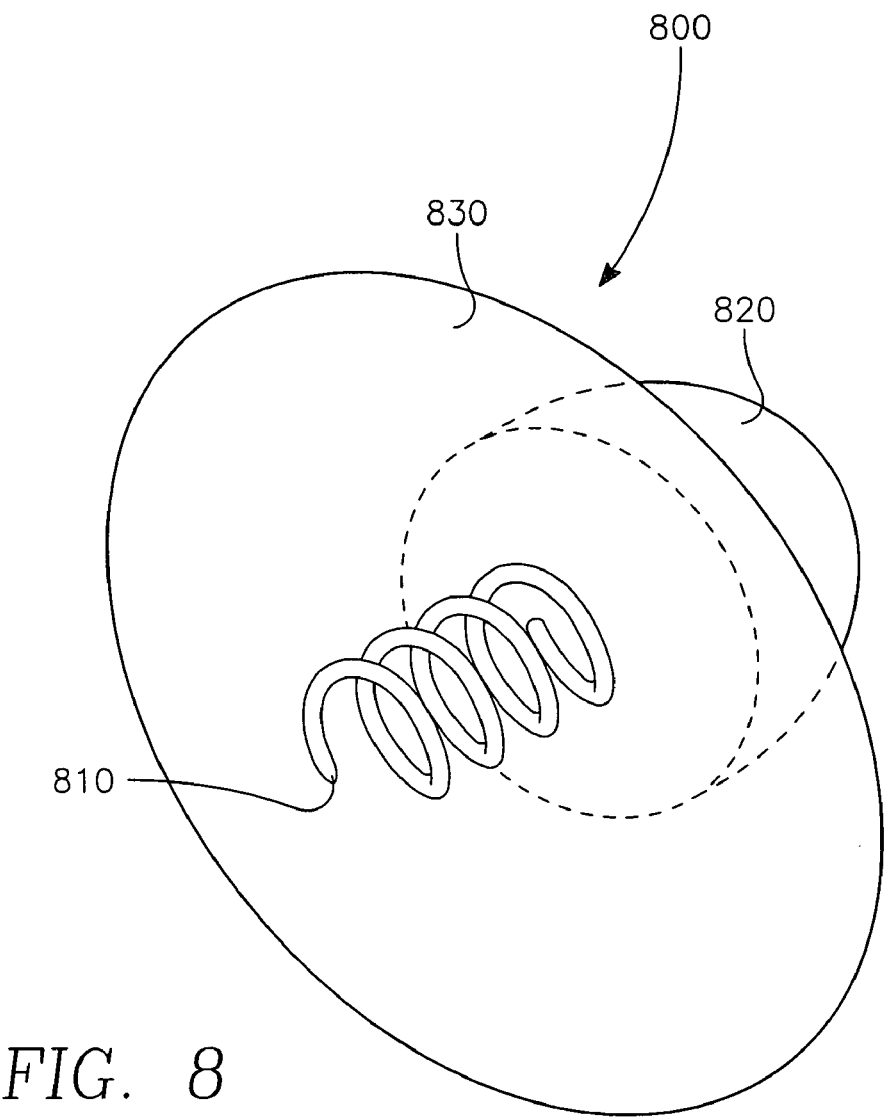
FIG. 8 shows a perspective view of a screw in button type satellite pacemaker.
Figure 9:
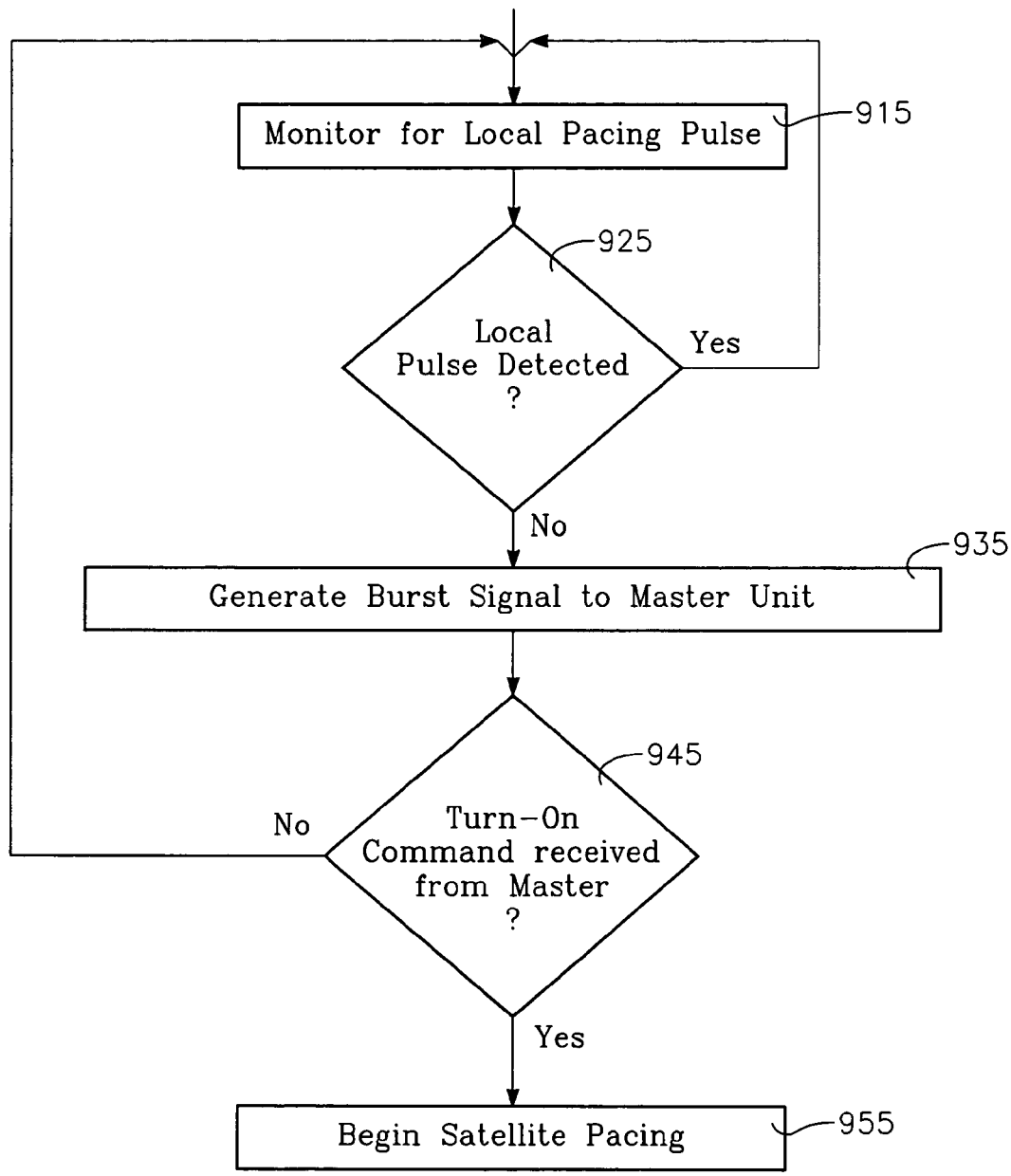
FIG. 9 is a flow diagram of a possible implementation in accordance with the present invention.

Failsafe Satellite Pacemaker System (FIGS. 7-9)

FIG. 7 shows a perspective view one possible embodiment in accordance with the present invention. Multiple satellite pacemakers 706*a-k* are secured into the left side of the heart 708. The number and distribution of satellite pacing units 706*a-k* is not limited to what is illustrated in FIG. 7 but rather is selected to provide effective pulse delivery corresponding to the desired therapy.

An example of one potential type satellite pacing unit is shown in FIG. 8. FIG. 8 shows a perspective view of a screw in button type satellite pacemaker 800. The example satellite pacemaker 800 is shown with a screw-in helix electrode 810 which extends from a case 820 through a optional skirt 830. The skirt 830 may be DACRON, or other material which facilitates in-growth fixation. The satellite pacing units 706*a-k* are not limited to this type, but instead may be attached to the exterior of the heart and/or have electrodes secured with the exterior of the heart by any known means. An additional example is disclosed in application Ser. No. 10/964,910, by Nabutovsky et al., entitled TISSUE CONTACT FOR SATELLITE CARDIAC PACEMAKER, filed Oct. 13, 2004; herein incorporated by reference in its entirety.

In some implementations, each of the multiple satellite pacemakers 706*a-k* will monitor for a local pacing pulse, a pulse very close to the sending satellite pacemaker. The local pacing pulse is distinguished from a native R-wave by the narrowness of the pulse. It would also be distinguishable from the pacing in the right ventricle apex by the amplitude of the pulse. If there is sensing of the right ventricle pacing pulse, then the method could be modified to ignore that second lower amplitude R-wave pulse. If a local pulse is detected, then a satellite pacemaker determines that one of the other satellite pacemakers is providing the necessary pacing pulse, and it continues to monitor.

If a local pulse is not detected when expected, i.e. within an escape interval, another satellite pacemaker will begin pacing. In some embodiments, this may occur at the direction of the master pacemaker 702, after the master pacemaker 702 is informed by a satellite pacemaker that no local pulse was detected. After a satellite pacemaker informs the master pacemaker that no local pulse was detected, the master pacemaker 702 will command one of the satellite pacemakers 706*a-k* to begin surrogate satellite pacing. It may select the satellite pacemaker that informed it of the absence of the local pacing pulse, or it may select one of the other satellite pacemakers 706*a-k* based on expected battery life or other factors. The selected satellite pacemaker may continue to deliver pacing pulses until its battery level is depleted.

In some embodiments, if a local pulse is not detected when expected, the satellite pacemaker will begin pacing without being directed by a master pacemaker 702. This may be accomplished by providing the satellite pacemakers with control circuitry constructed/programmed, to automatically generate a pacing pulse after waiting an escape interval in which there was no pacing pulse, or intrinsic pacing sensed. To avoid collision of pacing pulses by multiple satellite pacemakers 706*a-k*, each satellite pacemaker 706*a-k* is programmed to cause a delay in the generation of a pacing pulse by a unique amount. For example, each satellite pacemaker could delay a unique amount within a range of 0.1 to 39.9 milliseconds beyond the escape interval before initiating a pacing pulse. The specific range may be selected based on the number of satellite pacemakers.

In one embodiment, this may be implemented by providing each of the satellite pacemakers 706*a-k* with a random number generator. If no local pulse, or intrinsic pacing is sensed, a random number is generated within some range, 0.1 to 39.9 for example, by each of the satellite pacemakers 706*a-k*. In this way each satellite pacemaker determines its own unique delay amount beyond the escape interval.

Any of the satellite pacemakers 706*a-k* may assume pacing responsibility. The satellite pacemaker with the shortest delay would begin pacing. Once this local pacing is detected, the other satellite pacemakers would inhibit pacing pulse generation. The satellite pacemaker that begins pacing may then continue pacing until its battery is depleted.

In some implementations, it is possible to have the escape interval and the delay period combined so that each satellite pacemaker waits a unique escape interval. In such a case, the unique escape interval would be a single value which included some escape interval plus a unique delay period. Thus, in either case, each satellite pacemaker waits an escape interval and a unique delay interval before initiating pacing.

In certain embodiments, the particular satellite pacemaker that will assume pacing, for example 760a, may broadcast a message via wireless communication 711 to the other satellite pacemakers 706b-k to inform the other satellite pacemakers 706b-k that it will assume pacing responsibility.

In some embodiments, the pacing satellite pacemaker 706a communicates its expected longevity in maintaining pacing. The expected longevity is typically based on an estimate of battery life. In response, some or all of the other satellite pacemakers 706b-k could enter a low power state to conserve power until the pacing satellite pacemaker is exhausted. Thus, the pacing satellite pacemaker could cause some or all of the other satellite pacemakers 706b-k to hibernate, either by instructing each of the other satellite pacemakers 706b-k to power off, or by allowing each of them to determine how long they should be in the low power state in response to the longevity estimate of the pacing satellite pacemaker.

For example, if the pacing satellite pacemaker 706a estimates that it can maintain pacing for another 15 months, it could command some or all of the other satellite pacemakers 706b-k to turn off for 7 months, for example. The duration in the off state may be selected to ensure that there is a very high confidence that the pacing satellite pacemaker 706a can maintain pacing output for the selected duration. The duration for the low power state for some, or all, of the other satellite pacemakers 706b-k can vary, and may be different for some, or all, of the other satellite pacemakers.

In this way, the non-pacing satellite pacemakers can conserve batteries and automatically take over for the pacing satellite pacemaker when the pacing satellite pacemaker 706a fails.

Figure 10:
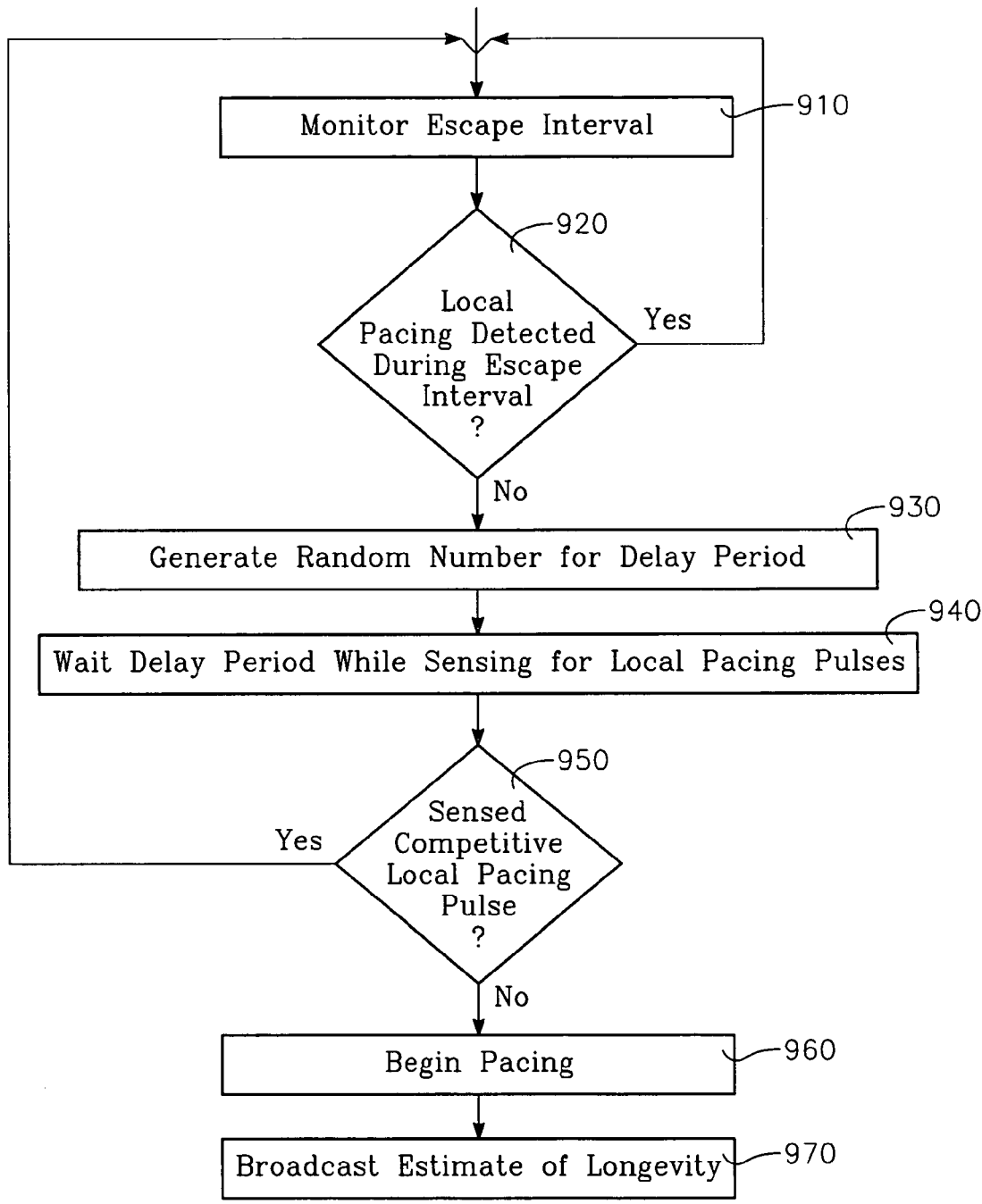
FIG. 10 is a flow diagram of a possible implementation in accordance with the present invention.

FIGS. 9 and 10 are flow charts showing possible implementations in accordance with the present invention. The implementations may be programmed in software and executed by a microcontroller in some embodiments. In other embodiments, they may be implemented in hardware, or in various combinations of hardware and software. The implementations of FIGS. 9 and 10 may be utilized separately, or may be combined together in part or in whole.

In the implementation of FIG. 9, a satellite pacemaker monitors 915 for a local pacing pulse. If a local pulse is detected, a satellite pacemaker then knows that its neighbor satellite pacemaker is functioning properly. If a local pulse is not detected 925, i.e. for an escape interval, the satellite pacemaker generates 935 a signal to the master pacemaker. The signal may be a strong burst signal from the satellite pacemaker to the master pacemaker informing the master pacemaker that its neighbor is not functioning and/or to request permission to begin satellite pacing. The master pacemaker may respond with a turn-on command. If a turn-on command is received 945 from the master pacemaker, the satellite pacemaker begins pacing 955. In some implementations, it may continue until its battery is depleted. If a turn-on command is not received by a satellite pacemaker, that satellite pacemaker will return to monitoring.

In the implementation of FIG. 10, the satellite pacemakers monitor for an escape interval 910 for a local pacing pulses. If a local pacing pulse is detected in the escape interval 920, each monitoring satellite pacemaker continues to monitor for the next escape interval 910. If a satellite pacemaker has not detected a local pacing pulse during the escape interval 920, each monitoring satellite pacemaker generates a random number for a delay period 930. Each satellite pacemaker then waits its unique delay period while sensing for a pacing pulse 940. If no competitive pacing pulse is sensed 950, a satellite pacemaker begins pacing 960.

In certain optional implementations, the satellite pacemaker that begins pacing may then broadcast an estimate of its longevity 970 to the other satellite pacemakers. In some implementations, the satellite pacemaker that begins pacing may broadcast a command to hibernate, which may include a duration, to the other satellite pacemakers, based on its longevity and/or other factors related to system health.

In one implementation, the satellite pacemakers will ensure satellite pacing by themselves if the master pacemaker fails to establish satellite pacing. Thus, in certain optional embodiments, the satellite pacemaker implementation of FIG. 10 can act as a backup to, or failsafe for the implementation of FIG. 9. For example, if wireless communication between the master pacemaker and the satellite pacemakers is impacted for some reason, the implementation of FIG. 10 can ensure satellite pacing continues.

Although shown in FIG. 7 with a hybrid wire/wireless system, certain embodiments may be completely wireless (not shown). The right side, as well as the left side, of the heart may be stimulated with the wireless satellite pacemakers system above if desired. Thus, a completely wireless system is possible in certain embodiments. Furthermore, the failsafe wireless system disclosed herein is not limited in its application, and may be utilized for various therapies, as a supplement, or a replacement for conventional wired systems.

In certain embodiments, a wireless link (not shown in FIG. 7) between the satellite pacemakers 706a-k and the leaded pacemaker 702 is not necessary. The satellite pacemakers 706a-k may operate autonomously in some embodiments. The satellite pacemakers 706a-k may arbitrate which satellite pacemaker will provide pacing pulses and then communicate between themselves. In certain embodiments, the satellite pacemakers may communicate between themselves prior to assuming pacing responsibility. Thus, in some embodiments the satellite pacemakers 706a-k are capable of autonomously selecting which of the satellite pacemakers 706a-k will deliver pacing pulses if no pacing pulses are detected by the satellite pacemakers 706a-k.

One advantage of certain embodiments is that because the distance between satellite pacemakers is closer than between a master pacemaker 702 and the satellite pacemakers 706a-k, lower power communication is possible. This allows the satellite pacemakers to conserve battery power.

As can be appreciated a wide variety of techniques can be implemented consistent with the principles of the invention and no attempt is made herein to describe all possible embodiments and implementations. Although described primarily with reference to congestive heart failure, the principles of the invention are applicable to other implanted cardiac stimulation devices as well, such as pacemakers without congestive heart failure therapy capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. An implantable failsafe pacemaker system comprising:
   a. a plurality of satellite pacemakers adapted to be mounted to an exterior of a heart;
   b. each of the plurality of satellite pacemakers being capable of sensing and delivering pacing pluses to the heart via at least one electrode; and
   c. each of the plurality of satellite pacemakers comprising control circuitry configured to wait a unique delay period beyond an escape interval and to begin pacing if no local pacing pulse from another one of the plurality of satellite pacemakers is detected during the escape interval or the delay period.

2. The failsafe pacemaker system of claim 1 wherein each of the plurality of satellite pacemakers comprise a wireless transceiver and is configured so that when one satellite pacemaker of the plurality of satellite pacemakers assumes pacing, the one satellite pacemaker transmits a wireless communication to others of the plurality of satellite pacemakers comprising information based on an anticipated longevity of the one satellite pacemaker.

3. The implantable pacemaker system of claim 2 wherein each of the plurality of satellite pacemakers are adapted to enter a low power state in response to the wireless communication by the one satellite pacemaker.

4. The implantable pacemaker system of claim 3 wherein each of the plurality of satellite pacemakers further comprise a random number generator to provide the unique delay period.

5. The implantable pacemaker system of claim 3 wherein each of the plurality of satellite pacemakers further comprise a preprogrammed unique delay period.

6. The implantable pacemaker system of claim 1 wherein each of the plurality of satellite pacemakers further comprise a random number generator capable of providing the unique delay period.

7. The implantable pacemaker system of claim 1 wherein each of the plurality of satellite pacemakers further comprise a preprogrammed unique delay period.

8. The implantable pacemaker system of claim 1 further comprising a pacemaker comprising a lead adapted for implantation within a right side of a heart.

9. The implantable pacemaker system of claim 8 wherein the plurality of satellite pacemakers are adapted for being attached to a left side of the heart.

10. The implantable pacemaker system of claim 1 wherein the at least one electrode is adapted to secure a satellite pacemaker to the heart.

11. An implantable failsafe pacemaker system comprising:
    a. a plurality of satellite pacemakers each of the plurality of satellite pacemakers being capable of sensing and delivering pacing pluses via at least one electrode mounted at an exterior of a heart;
    b. each of the plurality of satellite pacemakers being adapted for wireless communication between each other of the plurality of satellite pacemakers; and
    c. each of the plurality of satellite pacemakers including a processor comprising programmed executable instructions, the programmed executable instructions comprising:
       i) monitoring an escape interval after a last local pacing pulse for a next local pacing pulse;
       ii) waiting a delay period beyond the escape interval specific for each satellite pacemaker; and
       iii) providing surrogate pacing pulses after waiting the delay period if no pacing pulse is detected from another one of the plurality of satellite pacemakers within the escape interval and within the delay period.

12. The implantable pacemaker system of claim 11 wherein the executable instructions further comprise providing a wireless communication to others of the plurality of satellite pacemakers, the wireless communication comprising information based on an anticipated longevity associated with providing the surrogate pacing pulses.

13. The implantable pacemaker system of claim 12 wherein providing the wireless communication comprises providing the anticipated longevity.

14. The implantable pacemaker system of claim 12 wherein providing the wireless communication comprises providing a hibernation instruction to the others of the plurality of satellite pacemakers.

15. The implantable pacemaker system of claim 14 wherein providing the wireless communication further comprises providing a hibernation duration to the others of the plurality of satellite pacemakers.

16. The implantable pacemaker system of claim 14 wherein the executable instructions further comprises determining a hibernation duration in response to the wireless communication.

17. The implantable pacemaker system of claim 11 wherein the executable instructions further comprises instructing others of the plurality of satellite pacemakers to hibernate in combination with providing the surrogate pacing pulses.

18. The implantable pacemaker system of claim 17 wherein the executable instructions further comprise providing a hibernation duration instruction to the others of the satellite pacemakers.

19. The implantable pacemaker system of claim 17 wherein the executable instructions further comprise providing anticipated longevity information to the others of the satellite pacemakers.

20. The implantable pacemaker system of claim 11 wherein the executable instructions further comprise generating a random number within a range for use in determining the delay period.

21. The implantable pacemaker system of claim 11 wherein each satellite pacemaker comprises a preprogrammed unique delay period.

22. The implantable pacemaker system of claim 11 wherein each of the plurality of satellite pacemakers comprises an electrode capable of being inserted into the exterior wall of the heart.

* * * * *